United States Patent
Meyers et al.

(10) Patent No.: US 12,337,178 B2
(45) Date of Patent: Jun. 24, 2025

(54) PAIRING VAGUS NERVE STIMULATION WITH EMG-CONTROLLED FUNCTIONAL ELECTRICAL STIMULATION TO ENHANCE NEUROPLASTICITY AND RECOVERY

(71) Applicant: Battelle Memorial Institute, Columbus, OH (US)

(72) Inventors: Eric Meyers, Columbus, OH (US); Michael Darrow, Columbus, OH (US); David Friedenberg, Worthington, OH (US); Lauren Wengerd, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 469 days.

(21) Appl. No.: 17/698,350

(22) Filed: Mar. 18, 2022

(65) Prior Publication Data

US 2022/0296901 A1 Sep. 22, 2022

Related U.S. Application Data

(60) Provisional application No. 63/163,237, filed on Mar. 19, 2021.

(51) Int. Cl.
| | |
|---|---|
| *A61N 1/36* | (2006.01) |
| *A61B 5/11* | (2006.01) |
| *A61B 5/256* | (2021.01) |
| *A61B 5/296* | (2021.01) |
| *A61N 1/04* | (2006.01) |

(52) U.S. Cl.
CPC .......... *A61N 1/36053* (2013.01); *A61B 5/11* (2013.01); *A61B 5/256* (2021.01); *A61B 5/296* (2021.01); *A61N 1/0484* (2013.01); *A61N 1/36003* (2013.01); *A61N 1/36135* (2013.01)

(58) Field of Classification Search
CPC .............. A61N 1/36053; A61N 1/0484; A61N 1/36003; A61N 1/36135; A61B 5/296; A61B 5/256; A61B 5/11
See application file for complete search history.

(56) References Cited

U.S. PATENT DOCUMENTS

| | | | |
|---|---|---|---|
| 8,700,145 B2 * | 4/2014 | Kilgard | A61N 2/006 607/45 |
| 8,706,241 B2 | 4/2014 | Firlik | |
| | | (Continued) | |

FOREIGN PATENT DOCUMENTS

| | | |
|---|---|---|
| EP | 3653260 A1 | 5/2020 |
| WO | 2021178914 A1 | 9/2021 |

OTHER PUBLICATIONS

Search Report and Written Opinion for International Application No. PCT/US2022/20920 dated Jun. 14, 2022.

(Continued)

*Primary Examiner* — Shirley X Jian
(74) *Attorney, Agent, or Firm* — McDonald Hopkins LLC

(57) ABSTRACT

A combined closed-loop functional electrical stimulation (FES) and Vagal nerve stimulation (VNS) therapy system for treating neurological injuries. Detected EMG signals are used to determine movement (or intended movement) of an extremity. FES is then delivered to help evoke the movement, and VNS is delivered to enhance neuroplasticity and recovery.

12 Claims, 3 Drawing Sheets

(56) References Cited

U.S. PATENT DOCUMENTS

2013/0041419 A1* 2/2013 Kilgard .............. A61N 1/36103
603/3
2020/0405188 A1 12/2020 Sharma et al.
2021/0031026 A1 2/2021 Simon et al.
2021/0038880 A1 2/2021 Ben-David et al.

OTHER PUBLICATIONS

Examination report in corresponding Australian patent application No. 2022240751, dated May 20, 2024.
Extended European Search Report in corresponding EP patent application No. 22772278.2, dated Jul. 30, 2024.

* cited by examiner

PAIRING VAGUS NERVE STIMULATION WITH EMG-CONTROLLED FUNCTIONAL ELECTRICAL STIMULATION TO ENHANCE NEUROPLASTICITY AND RECOVERY

CROSS-REFERENCE TO RELATED APPLICATIONS

This application claims priority to U.S. Provisional Patent Application No. 63/163,237 filed on Mar. 19, 2021, the entirety of which is incorporated herein by reference.

BACKGROUND

Vagal nerve stimulation (VNS) has recently emerged as a new stroke therapy for accelerating recovery of motor skills in people with stroke by helping the brain re-organize neural connections more effectively. However, the therapy currently requires patients to be in intensive physical rehabilitation in a clinic for weeks, which can be prohibitively costly and time consuming. Additionally, the therapy requires observation of the patient by a clinician to manually activate the VNS during observed arm and hand movements.

Similarly, functional electrical stimulation (FES) is an adjunctive to rehabilitation after neurological injuries, such as stroke and spinal cord injury. During FES therapy, patients attempt a functional movement with their affected limb, and then a clinician triggers electrical stimulation of nerves related to the associated musculature to produce the attempted movement. FES therapy can be used for patients to regain motor control where neural connections have been lost. In other words, FES therapy stimulates nerves 'downstream' from the broken connection and allows the stimulator to serve as an artificial replacement for the brain.

BRIEF SUMMARY

According to one example, the present disclosure relates to a stimulation system. The system may include one or more sensors configured to detect a physiological signal in response to a user moving an extremity. The system may include a Vagal nerve stimulator. The system may include a functional electrical stimulator. The system may include a processor configured to selectively control delivery of one or both of the Vagal nerve stimulator or the functional electrical stimulator based on the detected physiological signal.

According to another example, the present disclosure relates to a stimulation method. The method may include detecting, by one or more sensors, a physiological signal in response to a user moving an extremity. The method may include selectively controlling, by one or more processors, delivery of one or more of vagus nerve stimulation or a functional electrical stimulation, wherein the sensors are configured to deliver the one or more of vagus nerve stimulation or a functional electrical stimulation based on the detected physiological signal.

According to still another example, the present disclosure relates to a computer readable storage medium comprising computer program code instructions, being executable by a computer, for: detecting a physiological signal in response to a user moving an extremity; and selectively controlling delivery of one or more of vagus nerve stimulator or a functional electrical stimulator based on the detected physiological signal.

According to still another example, the present disclosure relates to a system comprising: at least one physiological sensor configured to detect a physiological signal in response to a user moving an extremity; a Vagal nerve stimulation (VNS) system; a functional electrical stimulation (FES) system; and a processor configured to selectively control delivery of one or both of VNS via the VNS system or FES via the FES system based on the detected physiological signal.

In various embodiments of the above example, the processor is further configured to: determine a movement of the extremity based on the detected physiological signal, determine whether the movement of the extremity was correctly performed based on the detected physiological signal, and control the VNS system to stimulate the Vagus nerve when the movement of the extremity was correctly performed, and control the VNS system to withhold stimulating the Vagus nerve when the movement of the extremity was not correctly performed; the processor is configured to control the VNS system to stimulate the Vagus nerve within ten seconds of the movement being correctly performed; the processor is further configured to: determine an intended movement of the extremity based on the detected physiological signal, and control the FES system to stimulate muscles associated with the intended movement, thereby evoking the intended movement; the processor is further configured to: determine an intended movement of the extremity based on the detected physiological signal, control the FES system to stimulate muscles associated with the intended movement, thereby evoking the intended movement, and control the VNS system to stimulate the Vagus nerve within ten seconds of controlling the FES system evoking the intended movement; the processor is further configured to: instruct the user to move the extremity; the processor is further configured to: determine a movement of the extremity based on the detected physiological signal, compare the determined movement to the instructed movement, and control the VNS system to stimulate the Vagus nerve when the determined movement matches the instructed movement, and control the VNS system to withhold stimulating the Vagus nerve when the determined movement does not match the instructed movement; the system further comprises: a wearable garment, the wearable garment comprising a plurality of electrodes of the at least one physiological sensor and the FES system; the at least one physiological sensor and the FES system share at least one electrode of the wearable garment; the at least physiological one sensor comprises an electromyography (EMG) sensor; and/or the VNS system and the FES system are electrically isolated from each other.

According to still another example, the present disclosure relates to a method comprising: detecting a physiological signal in response to a user moving an extremity; determining the movement of the extremity intended or completed by the user; and controlling delivery of one or both of Vagal nerve stimulation (VNS) or functional electrical stimulation (FES) based on the determined movement.

In various embodiments of the above example, the method further comprises: determining whether the movement of the extremity was correctly performed based on the detected physiological signal, and controlling the delivery of VNS to stimulate the Vagus nerve when the movement of the extremity was correctly performed, and controlling the delivery of VNS to withhold stimulating the Vagus nerve when the movement of the extremity was not correctly performed; the VNS is delivered thereby stimulating the Vagus nerve within ten seconds of the movement being correctly performed; the method further comprises: controlling the delivery of FES to stimulate muscles associated with the determined intended movement, thereby evoking the intended movement; the method further comprises: controlling the delivery of FES to stimulate muscles associated with the determined intended movement, thereby evoking the intended movement, and controlling the delivery of VNS to stimulate the Vagus nerve within ten seconds of controlling the delivery of FES evoking the intended movement; the method further comprises: instructing the user to move the extremity; and/or the method further comprises: determining the movement of the extremity based on the detected physiological signal, comparing the determined movement to the instructed movement, and controlling the delivery of VNS stimulating the Vagus nerve when the movement of the extremity was correctly performed, and control the delivery of VNS withholding stimulating the Vagus nerve when the movement of the extremity was not correctly performed.

DETAILED DESCRIPTION

Figure 1:
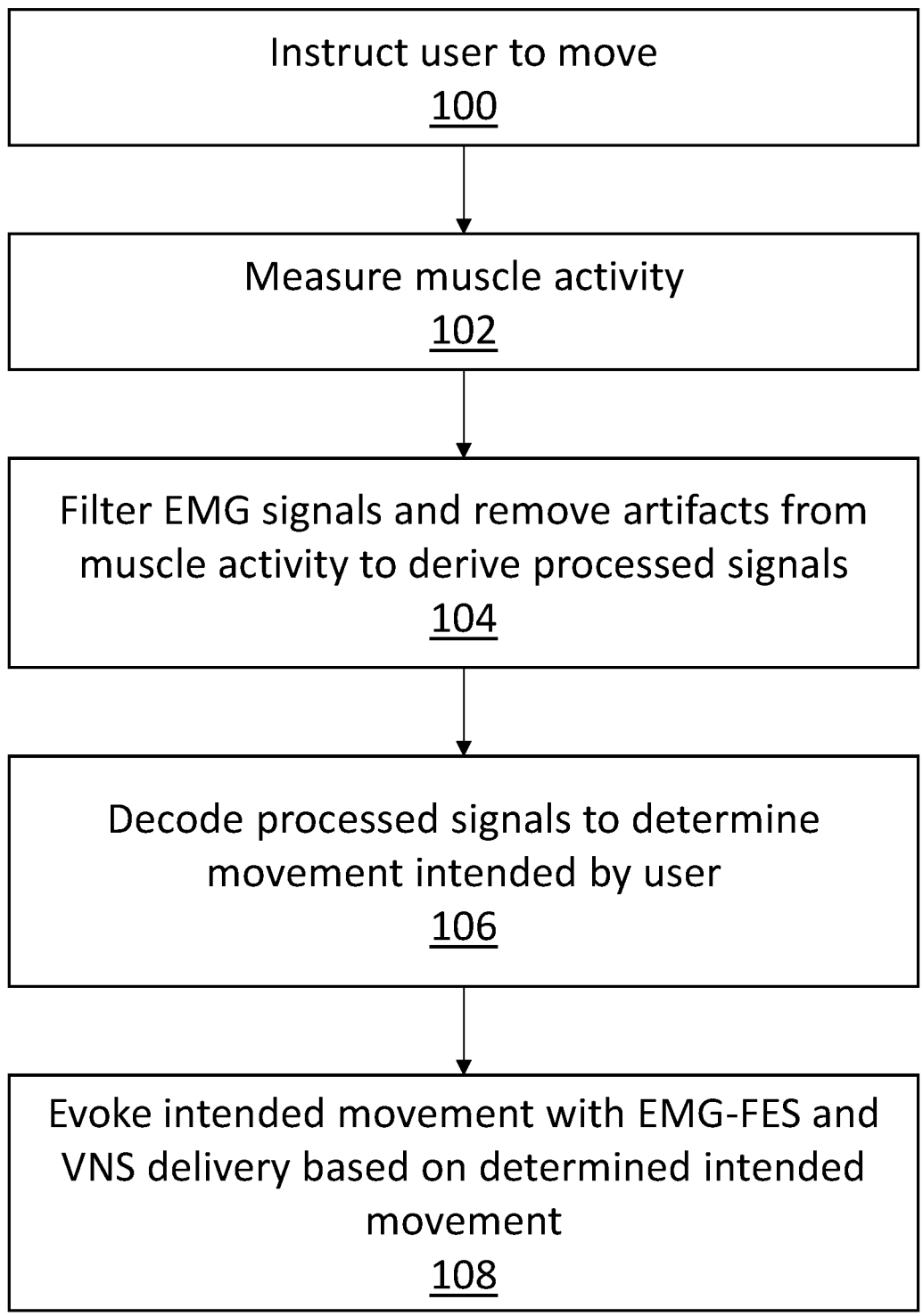
FIG. 1 illustrates an example therapy method according to the present disclosure.

Stroke remains a leading cause of long-term disability in the United States. While medical advances have led to decreased stroke mortality rates over the past decade, the number of people living with the devastating consequences of stroke continues to rise. As a result, an increased number of stroke survivors are living with upper extremity hemiparesis and it is estimated that over 50% of stroke survivors continue to require assistance with instrumental activities of daily living (e.g. meal preparation) six months post-stroke. There is thus a need to develop technologies that maximize the functional use of extremities of adult stroke survivors.

Vagal nerve stimulation enhances recovery after neurological injury through brief electrical stimulation of the Vagus nerve paired with movements of the arm and hand (or other extremity). Functional improvements mediated through VNS after stroke are paralleled by reorganization in corticospinal pathways, indicating that VNS enhances functional recovery by facilitating synaptic plasticity in spared motor networks. Electrical stimulation of the vagus nerve engages neuromodulatory systems in the brain that release chemicals, called neuromodulators, throughout the brain and are involved in facilitating neuroplasticity that underlie recovery after neurological injury. In view of this, pairing VNS with motor training is a clinically viable neuromodulation for treating neurological injuries that severely limit motor ability, such as severe stroke or spinal cord injury.

Currently, this VNS stimulation is performed by a clinician directing a user (e.g., a patient) through physical rehabilitation to perform a directed movement. When the user correctly performs the directed movement, the clinician manually triggers the VNS. The resulting stimulation reinforces the user's neural pathway when paired with the movement. In other words, stimulation in response to correct movement supports the user's re-organization of neural pathways. However, the current therapy limits VNS to clinical use with a physical therapist or like clinician. Furthermore, the delivery is subjectively based on visual inspection of the movement by the clinician. A still further limitation of current VNS therapy is reliance on a clinician to deliver stimulation during visual movement, such as the clinician pressing a button to deliver a 0.5 second stimulation train while the patient is actively moving.

Similar to when VNS stimulation is delivered, FES is delivered during an attempted movement to nerves associated with musculature that produce the movement. FES can be paired with cortically-driven motor intention (i.e. thinking of perming the movement) to improve recovery. Such combined FES therapy combines cortical activations and peripheral stimulation, and may apply Hebbian-based learning principles (e.g. fire together, wire together) to enhance experience-dependent neuroplasticity. In other words, the use of FES emphasizes the intended movement during rehabilitation, which would otherwise be much more limited due to the poor neural connections. Such emphasis adds (or improves) a sensory input to the recovery.

This FES stimulation may be triggered by a clinician, but such manual stimulation suffers from similar problems to those discussed above with VNS. Studies have used electromyography (EMG) for triggering FES by monitoring activity over a specific muscle, and then triggering FES once a predetermined threshold is reached. However, previous EMG-triggered FES systems do not effectively control FES based on the user's motor intentions. To address this shortcoming of previous EMG-triggered FES systems, brain-computer interfaces (BCI) may be used as FES controllers. BCI-FES systems operate by decoding brain activity during movement intent to trigger FES and evoke the intended movement. However, these BCI-FES systems also present numerous deficiencies. Current BCI-controlled FES systems utilize electroencephalography (EEG) to interpret brain activity. While commercial EEG systems are more user friendly, they suffer from poor signal quality and consequently, current EEG-controlled FES systems are limited to a single movement (e.g. hand open). Conversely, research-grade EEG systems can obtain higher resolution neural recordings and can thus decode a variety of hand and forearm movements, but they have limited clinical utility due to practical considerations, such as setup time and portability of the systems.

Using closed-loop stimulation systems and methods disclosed herein, the combination of FES therapy and VNS can lead to additive or supra-additive effects on neuroplasticity and recovery. Accordingly, the present disclosure relates to a combined and improved VNS and FES therapy system and method for treating users with neurological injuries affecting motor function. Such injuries may be the result of spinal cord injury, traumatic brain injury, peripheral nerve damage, stroke, and the like. In addition, the closed-loop stimulation systems and methods disclosed herein detect subthreshold movement intention (e.g., movement attempts that can not be visually observed but having muscle activity that can be detected through EMG recordings), and then stimulate both FES and VNS simultaneously to facilitate neuroplasticity. Moreover, the closed-loop stimulation systems and methods disclosed herein provide a transcutaneous auricular vagus nerve stimulation (taVNS) with FES therapy as a combined non-invasive neuromodulation solution to enhance neuroplasticity and recovery.

As used herein, the term "simultaneous" refers to the execution of FES and VNS within a time period in which VNS is still effective to achieve neuroplasticity and reinforce neural pathways associated with the movement evoked by FES. By way of example, VNS and FES are preferably executed within ten seconds of each other. According to one particular example, the execution of FES may be within a few hundred milliseconds of a determined intended movement and the execution of VNS occurs within ten seconds of the execution of FES. In other embodiments, the execution may of FES and VNS may be even closer in time, for example, within ten seconds, five seconds, or even within two seconds.

Briefly, according to the present disclosure, EMG signals are recorded from a user and those EMG signals are then used to simultaneously trigger the VNS and/or FES. Accordingly, control of VNS and FES delivery is shifted from the clinician so that the therapy can be performed remotely (e.g., at home, as tele-therapy, or the like) and does not require physical therapy in a clinic. Such VNS and FES therapy may thus be used across the continuum of care: sub-acute, acute, chronic, chronic at-home, and the like. The above-described EMG control of VNS and FES therapy is based on a closed-loop stimulation system and method, in which stimulation is controlled in response to a detected physiological state or parameter.

According to the example method of FIG. 1, a user is first instructed to perform a movement 100. This movement may be, for example, the opening/closing of a hand, the lifting of a lower/upper arm, or the like. The intended muscle activity of a user is then measured 102 by various sensors (e.g., EMG sensors) attached to the user. In one example, muscle activity may be detected by one or more sensors in a wearable garment, such as a sleeve (described in more detail below). Following measurement, the method may include filtering 104 signals from the sensors and removing artifacts. These artifacts may be from signal detection and/or concurrent stimulation. For example, a blanking method may be implemented to remove artifacts, such as FES-induced artifacts. The sensor data may be based on, for example, 100 ms of recorded EMG data. The 100 ms EMG data may be continually analyzed on a rolling basis. In one example, a root mean squared value of the EMG data across all EMG sensors is determined for each rolling 100 ms data set.

The resulting processed signals are then decoded 106 to determine the user's intended movement. In some embodiments, this analysis may be performed by a trained machine learning system. The training data for such a system may comprise EMG sensor data associated with corresponding properly executed movements. In this manner, the machine learning system is trained to recognize the EMG signals that correspond to possible movements, so that EMG signals of a detected movement can be compared with the expected EMG signals for an instructed movement. The EMG signals for each movement may be differentiated, for example, by the use of a plurality of EMG sensor channels associated with different muscles, for example, as discussed below with respect to a wearable garment such as a sleeve. In this manner, because different groups of muscles are activated at different levels and times for different movements, corresponding EMG signals associated with those muscle groups may be analyzed to determine the movement being performed by the user. Those determined movements can then be compared to the instructed movement to determine whether the user performed the correctly instructed movement.

Such a comparison may be made by the trained machine learning system (e.g., configured to classify the signals as a particular movement) or by performing a statistical comparison or like pattern matching method, and identifying the movement to which the detected signals most closely correspond. Then, if the identified movement corresponds to the instructed movement, the system can determine that the correct movement was performed. In other embodiments, the detected signals may be compared only to signals expected from the instructed movement, and a determination of whether the movement was correctly performed may be made if the signals match at a predetermined threshold level. In some embodiments, the trained machine learning system may comprise a class classifier for each of a plurality of possible instructed movements such that each classifier is trained to identify whether input signals correspond to the movement the classifier is trained to identify. Depending on the determinations being made, the classifier may be a one-class, two-class, or other multi-class classifier. Thus, the detected signals are input to the classifier trained to determine the instructed movement and the output of the classifier (or each class of the classifier) can be a binary indication as to whether the instructed movement was actually performed.

Similarly, a regression algorithm may be used with a threshold bound to determine movements. For example, joint angles (e.g., of the fingers) may be identified via a regression analysis of EMG or other sensor signals (e.g., accelerometers or like motion or position sensors in a glove worn by the user). A movement (such as hand extension) may then be determined based on an interpretation of those identified angles relative to the threshold. For example, a hand extension may be determined when the angles of the fingers (or other joints) approach 180 degrees, exceeding a predetermined threshold (e.g., set at 120 degrees).

It should also be understood that intended movements can be determined without a priori knowledge of the intended movement (e.g., by recognizing temporal and spatial patterns from sensors of different muscles). In other words, the determination can be made without knowing the instructed movement the user was attempting to perform. In one embodiment, such an operation may be performed by comparing the detected sensor data to that of known movements, and identifying the intended movement as the one having sensor data that most closely matches the detected sensor data from the user. The determination of whether the movement was properly performed may then be made if the similarities between the detected movement data and the known movement data are within a predetermined range (the detected data and expected data match at a predetermined threshold level). In other embodiments, the measured data may be input to a machine learning system trained to classify the detected sensor data as corresponding movements. In some embodiments, a confidence level, where the confidence level of the classification can be compared to a predetermined threshold to determine whether the movement was properly performed. For example, a high level of confidence indicates that the detected movement likely corresponds to a known movement. When inferring that the user intended to perform the known movement, the movement may be identified as successfully performed. In contrast, a low level of confidence suggests that the detected movement does not correspond to any known movements and thus was likely a failure.

Further examples of systems and methods for the above analysis and control of stimulation are described in U.S. patent application Ser. No. 17/339,309 filed on Jun. 4, 2021 and published as U. S Patent Publication No. 2021/0379372 on Dec. 9, 2021, the entirety of which is herein incorporated by reference.

Finally, the method includes simultaneous stimulation 108 of the corresponding muscles/muscle groups via FES to evoke the intended movement and VNS to reinforce the user's neural pathways, based on the detected intended movement. In some embodiments, VNS delivery may be limited for only the most positive type of neural activity exhibited by the user, thereby reinforcing and improving their best attempt regarding the intended movement and avoiding potential saturation that may be caused by excessive VNS application. Of course, only one of FES and VNS may be applied, rather than both simultaneously.

Figure 2:
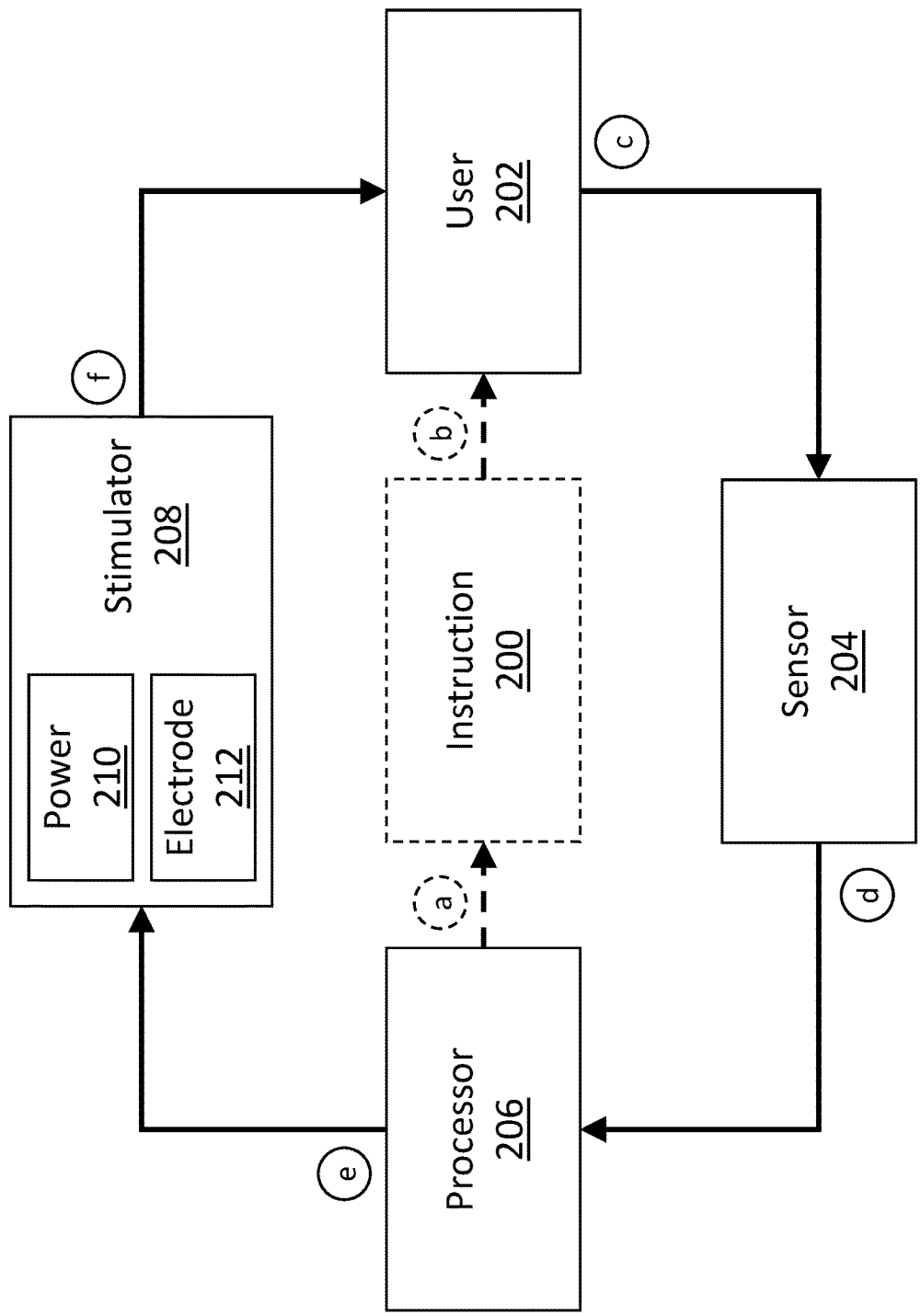
FIG. 2 illustrates an example therapy system according to the present disclosure.
Figure 3:
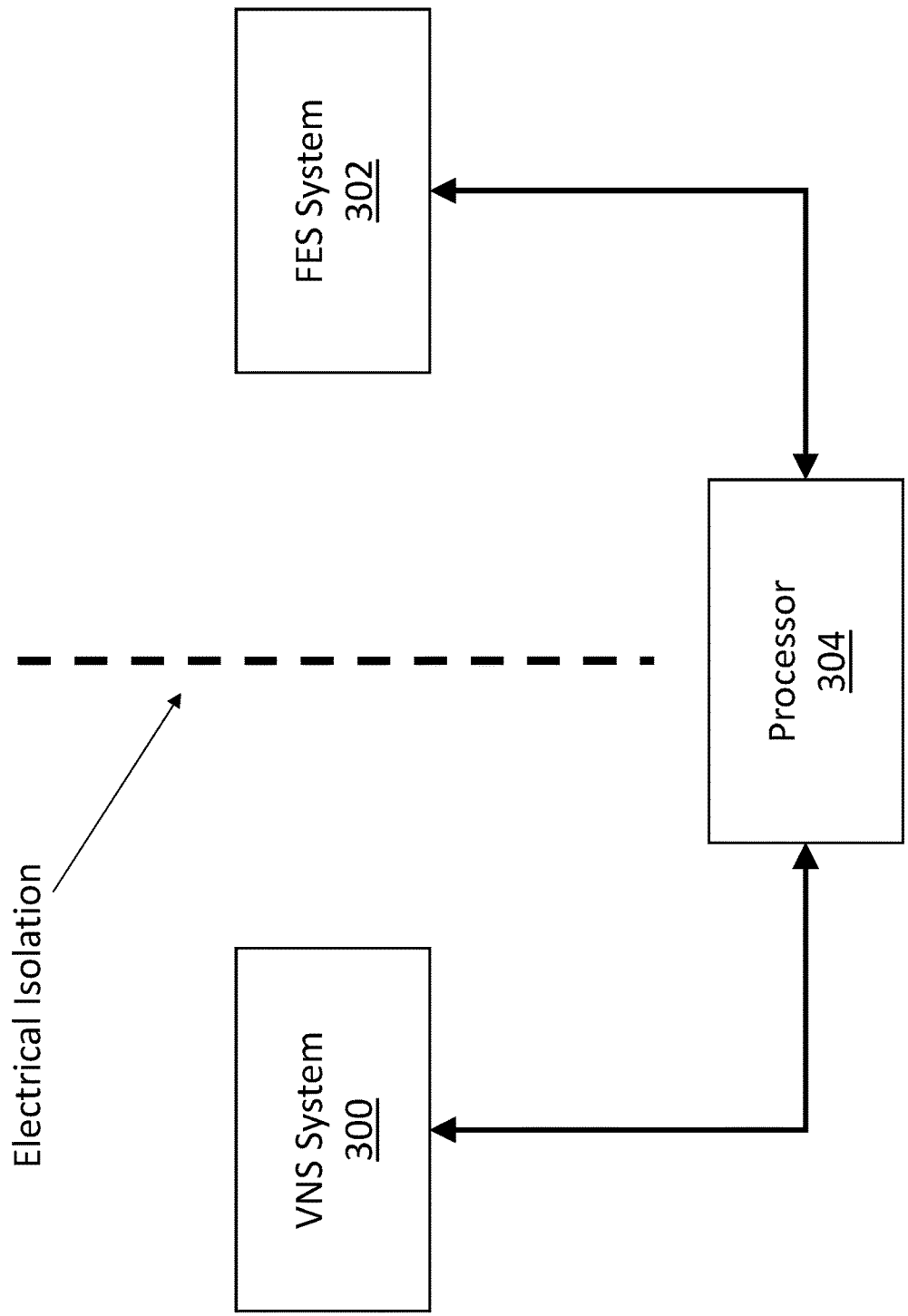
FIG. 3 illustrates an example combined Vagal nerve stimulation (VNS) and functional electrical stimulation (FES) therapy system according to the present disclosure.

Example closed-loop stimulation systems of the present disclosure that may implement the method of FIG. 1 are illustrated in FIGS. 2 and 3. Particularly, FIG. 2 illustrates an example closed-loop stimulation therapy system according to the present disclosure. This system configuration may correspond to either an FES or VNS system. The system generally includes a sensor 204, processor 206, and stimulator 208, the stimulator further having a power source 210 and electrode 212. Although FIG. 1 illustrates single instances of the components, system may include any number of components.

According to such a system (and corresponding method), an instruction 200 is first given to a user 202 to perform a movement of an extremity (steps (a) and (b)), such as an arm or hand. In some embodiments, the instruction may be given by virtual direction. For example, a processor 206 may execute a software application that outputs visual or audible instructions 200 to the user 202 via an output device, such as a speaker or display screen. The output may be a simple direction, an illustration (e.g., video or images), and/or the like of the desired movement. The instructions 200 may be pre-programmed, or may be dynamically generated based on the user's progress through therapy. The instructions 200 may also be generic to all users, or user-specific (e.g., generated specifically to address troublesome movements for each user 202 according to the user's needed therapy). In some embodiments, no instruction may be given. Embodiments without a given instruction permit delivering therapy to the user 202 during activities of daily living (ADL). Again, the processor 206 may identify movements a user 202 attempts to perform (e.g., lifting an arm to take an item off a shelf) based on the data, and then cause VNS delivery when determining that movement was properly performed. By enabling therapy during ADL, the user is further relieved of the costs and burdens associated with traditional therapy that requires clinical visits.

As the user 202 performs the instructed (or otherwise intended) movement (step (c)), at least one sensor 204 detects EMG signals from the user 202 (step (d)), which are supplied to the processor 206. In some embodiments, EMG sensors may be applied directly to the extremity performing the movement. The EMG sensors may also be applied to the user 202 as part of a sensor apparatus, for example, a sleeve having a plurality of EMG sensors/sensor channels therein arranged to detect signals from desired muscle(s) and/or muscle group(s). Such a sleeve may be of the type described in U.S. Patent Application Nos.: 1) Ser. No. 14/728,512 filed on Jun. 2, 2015 and issued as U.S. Pat. No. 9,884,179 on Feb. 6, 2018; 2) Ser. No. 15/578,816 filed on Dec. 1, 2017 and issued as U.S. Pat. No. 10,765,859 on Sep. 8, 2020 (based on PCT/US2016/035529 filed on Jun. 2, 2016); 3) Ser. No. 15/872,734 filed on Jan. 16, 2018 and published as U.S. Patent Publication No. 2018/0154133 on Jun. 7, 2018; 4) Ser. No. 16/877,554 filed on May 19, 2020; 5) 63/058,776 filed on Jul. 30, 2020; 6) 63/058,968 filed on Jul. 30, 2020; 7) Ser. No. 17/002,135 filed on Aug. 25, 2020 and published as U.S. Patent Publication No. 2020/040622 on Dec. 31, 2020; 8) Ser. No. 17/008,199 filed on Aug. 31, 2020 and published as U.S. Patent Publication No. 2020/0405188 on Dec. 31, 2020; and 9) Ser. No. 17/339,309 filed on Jun. 4, 2021 and published as U.S. Patent Publication No. 2021/0379372 on Dec. 9, 2021, the entireties of these applications being incorporated herein by reference. The at least one sensor 204 may also or instead detect other physiological parameters, such as an ECG, EEG, blood pressure, heart rate, blood oxygen saturation, and the like, for monitoring the user's 102 physiological state before, during, and/or after the VNS therapy.

The processor 206 then analyzes the detected physiological signals to determine whether the movement was properly performed, and/or to determine the physiological state of the user 202, as discussed above with respect to step 106 of FIG. 1. Accordingly, the processor 206 may be configured as the trained machine learning system, to perform the comparisons, to perform the regression algorithms, and the like.

For VNS therapy, when the processor 206 determines that the user 202 is performing or has performed the instructed movement, based on the physiological signals from the at least one sensor 204, the processor 206 causes (step (e)) the stimulator 208 to execute the stimulation therapy (step (f)); and conversely, when the processor 206 determines that the user is not performing the instructed movement, the processor may not allow the stimulator 208 to perform the VNS therapy. In other words, VNS therapy may be withheld when the user 202 performs a movement other than the instructed movement, so as to reinforce incorrect neural pathways. As suggested above, VNS is preferably delivered soon after the user performs the movement. For example, the system herein can deliver VNS within ten seconds of the patient performing the movement. In another example, the system can deliver VNS within five seconds or within two seconds of the patient performing the movement.

For FES therapy, when the processor 206 determines the intended movement, a corresponding FES stimulation therapy is executed by stimulator 208 to evoke the appropriate muscles and muscle groups to perform the desired movement. If VNS is paired with FES stimulation, the VNS is preferably delivered soon after the FES is applied. For example, the system herein can deliver VNS within ten seconds of the FES application. In another example, the system can deliver VNS within five seconds or within two seconds of the FES application. Further for FES therapy, it is noted that stimulation may be provided when or shortly after the instruction 200 is given to user 202, or when or shortly after any intended movement is detected. This is because, unlike VNS therapy which is intended to reinforce proper movements, FES therapy is intended to evoke those movements. Therefore, it is not necessarily possible to wait until those movements have fully occurred.

The stimulator 208 may comprise a power source 210 that provides, for example, an AC voltage or stimulation current from a current source (e.g., a bipolar current stimulator) or via capacitive discharge to an electrode 212, thereby performing the stimulation therapy (step (f)). The power source 210 may be controlled by the processor 206, according to the analysis described above. Such control may cause the power source 210 to output a stimulation voltage or current according to stimulation parameters and/or protocol in accordance with the VNS. These parameters may be predetermined and stored in a memory, or dynamically determined by the above-described or a like machine learning system, based on the detected movement and/or other detected physiological parameters from the at least one sensor 204. The stimulation parameters may be generic to all users 202, or to the specific user 202 being treated.

For example, VNS stimulation may be delivered at 0-3 mA at 0-1 kHz and a pulse width of 0-500 µs for a duration of 0-2 seconds. In one particular example, the VNS is delivered at 0.8 mA constant current charge balanced pulses at 30 Hz and a pulse width of 100 µs for 0.5 seconds. However, these are merely example stimulation parameters and are not intended to be limiting. For example, stimulation parameters may vary based on a severity of injury, strength of therapy, the type of electrode used, unique physiological features of the receiving user, and/or the like. Further, as noted above, the stimulation parameters may be dynamically changed based on the user or the therapy state. For example, increasing stimulation throughout a session (e.g., within a given day) could improve therapeutic benefit of the VNS therapy.

The electrode 212 of the stimulator 208 may be any electrode suitable for delivering stimulation therapies. For example, the electrode 212 may be an implanted electrode, such as a nerve cuff electrode around a portion of the Vagus (or other) nerve or muscle/group, or a flat electrode. In some embodiments, the electrode 212 may be a skin-surface electrode. In the case of an implanted electrode, the output of the power source 210 is supplied directly to the Vagus (or other) nerve or muscle/group via contact between the electrode 212 and the nerve. In the case of a skin-surface electrode, the electrode 212 is located on the skin surface of the user 202, and the output of power source 210 is applied to the Vagus (or other) nerve or muscle/group transcutaneously. The electrode 212 may be placed to deliver the therapy to any location along the nerve or intended muscle/group. In one example embodiment, the VNS therapy is delivered to the cervical Vagus nerve. In some embodiments, VNS stimulation may be delivered at the auricular branch of the Vagus nerve in the ear. Stimulation of the auricular branch at the ear is noninvasive and different than transcutaneous stimulation over the neck, which would activate the main Vagus nerve bundle.

In addition to the above, the stimulation electrode 212 may be the same as, or integrated with the electrode(s) comprising the at least one sensor 204. These electrodes 204, 212 may thus be integrated together in a wearable garment, such as the sleeve discussed above. For example, the sleeve may comprise a plurality of surface electrodes that serve as EMG sensor electrodes and FES stimulation electrodes. In other words, these EMG sensor electrodes may be those used to inform and control FES and VNS, and to provide the FES stimulation. Of course in other embodiments, separate EMG sensors may be utilized for FES and VNS, or FES may provide stimulation through different surface electrodes. These additional electrodes may be integrated with the wearable garment or separately affixed to the user.

In addition to controlling stimulation when the processor 206 determines that the user 102 is performing or has performed the instructed movement, stimulation may also be controlled based on a determined physiological state of the user 202 from the at least one sensor 204. For example, if the processor 206 determines that the user is experiencing an increased heart rate, blood pressure, or recognizes like stress indicators, the processor 206 may stop stimulation and/or the therapy session (e.g., by no longer instructing the user 202 to perform any movements). Similarly, if negative reactions to stimulation are detected, the processor 206 may stop the stimulation and/or therapy session or may adjust the stimulation parameters to a more appropriate level that does not induce the negative reaction. Such new stimulation parameters may be determined by a machine learning system of the processor 206, trained to output those new parameters based on the current stimulation parameters, the physiological state of the user 202 identified from the at least one sensor 204, and/or the like. In other words, the stimulation may be tuned based on physiological response/feedback to the stimulation.

The above description and FIG. 1 identify the processor 206 for analyzing EMG and other physiological signals as the same processor for instructing the user to perform a particular movement. In this manner, the processor 206 is aware of the instructed movement and thus the EMG signals/the user movement that should be detected. Further, such a system is more compact and self-contained. However, in other embodiments, the functions of the processor 206 may be embodied by multiple processors and/or distinct devices. For example, the processor associated with the given instruction 200 may be a user device, such as a mobile terminal or a home desktop computer, while the processor controlling stimulation may be part of the stimulator 208. In other embodiments, the therapy instructions 200 may be controlled by a clinician device or remote device (e.g., a central server), with the instruction 200 being displayed on a user device. In each of these instances, the processors are preferably in communication with each other. Such communication may be wired or wireless, and over a local or private network, or a global network such as the Internet or those for cellular communication.

Where processor 206 is embodied as multiple processors, those processors may be located locally, remotely, or in some combination thereof. For example, the clinician device may be remote from the user device and/or stimulator 208. Accordingly, the clinician may be located at a remote clinic while the user 202 is located at their home or other remote location. In such a configuration, the clinician may monitor the VNS therapy and/or direct the therapy by controlling the instructions 200 provided to the user 202, without the user 202 needing to be at the clinic with the clinician. In some embodiments, the analysis of physiological signals may be performed by a remote processor (e.g., a centralized server) in communication with a processor of the stimulator 208. Accordingly, the physiological signals are sent from a user device to a remote server for analysis and, when the correct movement is detected, the remote server may instruct the stimulator to perform the VNS. Such centralized analysis eases updates and training of the machine learning system that analyzes the physiological parameters, and reduces the processing burden on user-side devices, thereby reducing cost and size, and easing use.

In addition to the above, data collected from the at least one sensor 204 (step (d)), and the corresponding stimulation therapy outputs (step(f)), instructions 200 (steps (a) and (b)), can be stored, for example, in a remote database (e.g., a centralized server). Such data can be analyzed and used for further training of machine learning systems executed by the processor 206, and/or analysis of the user's 202 therapy progress. For example, such analysis can be used to improve the instructions 200 sent to a user by identifying which (instructed) movements a user continues to struggle to perform. Accordingly, instructions 200 may be given for movements which the user 202 is least successful in performing and which emphasize the neural pathways for performing those movements. The analysis may also be used to optimize VNS stimulation parameters for a given user 202. For example, the stimulator 208 may learn to utilize stimulation parameters/protocols for which the user 202 is most responsive. In one embodiment, stimulation parameters/protocols used in conjunction with movements the user 202 is most successful in performing may be identified as those the user 102 is most responsive to. Accordingly, those identified stimulation parameters/protocols may be utilized for VNS in response to instructed movements the user 202 performs less successfully. The stored data may also be used globally, rather than for user-specific uses. For example, optimum stimulation parameters may be identified for different populations (e.g., based on age or gender).

In embodiments where a machine learning system is utilized, the above-noted stored data may be used to train (or re-train) the machine learning system. Such 're-training' may occur continuously as data is collected and/or stored, or may be performed in batches at given intervals (e.g., once a week, once a month, once a year, and the like). The interval may be determined based on the frequency of data collection and storage, efficacy of existing systems, and the like.

Using the above-described sleeve and the sensors therein to trigger stimulation therapy enables therapy to be performed at home (or some whether other than a clinic or with a clinician) by the user 202. This allows neurological injury users to self-administer rehabilitation and receive stimulation therapy in their own home, without the expenses of intense clinician involvement and use of clinical facilities, because the stimulation therapy may be delivered without the traditionally required visual inspection/confirmation of the user movement by the clinician. Still further, using signals from the at least one sensor 204 to trigger the stimulation therapy rather than visual inspection reduces the variability, and increases the consistency, in stimulation delivery. In other words, while a clinician's determination of whether a movement is successfully performed is subjective, that determination is instead made by objective analysis of physiological signals. Further, whereas a clinician may take different amounts of time to identify movements and react by delivering the stimulation therapy, the objective analysis of sensor data and control by a processor enables repeated and consistent stimulation therapy delivery in response to a given user movement and state. Still further, because stimulation therapy delivery is based on the sensor data, analysis by a processor, and the stimulator, rather than a clinician, the user 202 is able to receive identical therapy both at a clinic and at home. As a result, further therapy repetitions may be performed by the user (e.g., throughout a day rather than a short therapy session). Similarly, such additional uses allow more collection of data for training of machine learning systems and improvements in the detection of movement and stimulation parameters.

When a user 202 wears the sleeve, muscle activity may be continuously recorded through electrodes positioned across an arm of the user 202. When a user 202 attempts a desired movement, the muscle activity may be used to predict movement intention. The sleeve may then deliver electrical stimulation to evoke the desired movement and simultaneously activate the stimulator 208 to release neuromodulators in the central nervous system and facilitate neuroplasticity and recovery. The system may be configured for use during complex rehabilitative exercises incorporating a plurality of forearm movements, including but not limited to, reaching to grasp and manipulate an object; pouring water; and using a spoon and fork. Without limitation, a plurality of forearm movements may include any number and/or type of: flexions (such as index, middle, ring, pinky, or thumb flexions); open or closed hand positions; partially open or closed hand positions; and grips (bottle grip, mug grip, pinch grip, paper grip, utensil such as fork/spoon/knife grip) that are partially or fully open or closed.

Using this system during rehabilitation can enhance long-term recovery. In addition, this system may be configured for use during goal-oriented tasks either in the clinic or at-home, and also to assist with ADL.

FIG. 3 illustrates an example integrated VNS and FES therapy system according to the present disclosure. FIG. 3 may reference and incorporate any components of the system explained above with respect to FIG. 2.

Briefly, as shown in FIG. 3, the integrated VNS and FES therapy system includes a VNS therapy system 300 (such as that described with respect to FIG. 2), an FES therapy system (also such as that described with respect to FIG. 2), and a processor 304. In some examples, the VNS system and FES system of the integrated system may share a common processor 304, such as illustrated in FIG. 3. Additionally, other elements of the therapy systems 302, 304 may be shared. For example, the sensors 204 of each system may be commonly used to detect physiological signals, and the processors 206 of each system may be integrated with the processor 304 of the integrated system. In one embodiment, both the VNS system and FES system use the same wearable garment (e.g., the sleeve discussed above) to detect physiological signals and deliver stimulation.

In some examples, the power source 210, stimulation electrodes 212, and/or other electrical components may be different for the VNS system and FES system to ensure electrical isolation therebetween. Electrically isolating each system mitigates the risk of electromagnetic interference during FES and/or VNS application. Such isolation may be realized by using different and isolated electrical lines, sources, grounds, and the like. In some embodiments, at least stimulation portions of the FES and VNS systems may be provided independently and communicate with each other wirelessly via BLUETOOTH or like communication protocols. Alternatively or additionally, the isolation may be realized by including barriers between the separate electrical elements of each system. Such barriers may include dielectric layers, pottings, sheaths, and the like.

As a consequence of simultaneous FES activation and VNS delivery, a plurality of benefits are advantageously achieved: 1) FES increases muscle activation and thus more effectively engages sensory and motor systems compared to conventional therapy, and simultaneously pairing it with a VNS train for neuromodulator release increases neuroplasticity effects of VNS; 2) Automated pairing of EMG with VNS can more precisely time motor intent and VNS activation, providing neuroplasticity-enhancing effects; 3) EMG can be measured and decoded and provide a sensitive control signal for VNS pairing, and thereby expanding access to more severely impaired spinal cord injury patients where visible motor intent is difficult to distinguish, such as in discomplete spinal cord injury patients; and 4) continuous, high-definition EMG data collected while using the system allows for remote monitoring of recovery during therapy, system performance, and adherence. Thus, the therapeutic potential of VNS and FES is realized while simultaneously addressing their limitations to deliver enhanced sensory and motor recovery.

While various features are presented above, it should be understood that the features may be used singly or in any combination thereof. Further, it should be understood that variations and modifications may occur to those skilled in the art to which the claimed examples pertain.

What is claimed is:

1. A system comprising:
   at least one physiological sensor configured to detect a physiological signal in response to a movement of an extremity intended by a user;
   a Vagal nerve stimulation (VNS) system;
   a functional electrical stimulation (FES) system; and
   a processor configured to selectively control delivery of one or both of VNS via the VNS system or FES via the FES system based on the detected physiological signal:
   wherein the VNS system is selectively controlled by:
      instructing the user to move the extremity;
      determining a movement of the extremity based on the detected physiological signal;
      comparing the determined movement to the instructed movement; and
      determining whether the determined movement matches the instructed movement based on the comparison; and
      controlling the VNS system to stimulate the Vagus nerve when the determined movement of the extremity matches the instructed movement, and controlling the VNS system to withhold stimulating the Vagus nerve when the determined movement of the extremity does not match the instructed movement, and
   wherein the FES system is selectively controlled by:
      determining an intended movement of the extremity based on the detected physiological signal; and
      controlling the FES system to stimulate muscles associated with the intended movement, thereby evoking the intended movement.

2. The system of claim 1, wherein the processor is configured to control the VNS system to stimulate the Vagus nerve within ten seconds of the movement being completed.

3. The system of claim 1, wherein the processor is further configured to:
   control the FES system to stimulate muscles associated with the intended movement, thereby evoking the intended movement; and
   control the VNS system to stimulate the Vagus nerve within ten seconds of controlling the FES system evoking the intended movement.

4. The system of claim 1, further comprising:
   a wearable garment, the wearable garment comprising a plurality of electrodes of the at least one physiological sensor and the FES system.

5. The system of claim 4, wherein the at least one physiological sensor and the FES system share at least one electrode of the wearable garment.

6. The system of claim 1, wherein the at least one physiological sensor comprises an electromyography (EMG) sensor.

7. The system of claim 1, wherein the VNS system and the FES system are electrically isolated from each other.

8. The system of claim 1,
   wherein the intended movement is the instructed movement, and
   wherein the determined movement of the extremity does not match the instructed movement.

9. A method comprising:
   detecting a physiological signal in response to a movement of an extremity intended by a user;
   determining the movement of the extremity based on the detected physiological signal; and
   selectively controlling delivery of one or both of Vagal nerve stimulation (VNS) or functional electrical stimulation (FES) based on the determined movement,
   wherein the VNS is selectively controlled by:
      instructing the user to move the extremity;
      comparing the determined movement to the instructed movement; and
      controlling the delivery of VNS to stimulate the Vagus nerve when the determined movement of the extremity matches the instructed movement, and controlling the delivery of VNS to withhold stimulating the Vagus nerve when the movement of the extremity does not match the instructed movement, and
   wherein the FES is selectively controlled by:
      determining whether the movement of the extremity was completed as intended by the user based on the detected physiological signal; and
      controlling the delivery of FES to stimulate muscles associated with the determined movement, thereby evoking the intended movement, when the determined movement was intended but not completed as intended by the user.

10. The method of claim 9, wherein the VNS is delivered thereby stimulating the Vagus nerve within ten seconds of the movement being completed.

11. The method of claim 9, further comprising:
    controlling the delivery of FES to stimulate muscles associated with the determined intended movement, thereby evoking the intended movement; and
    controlling the delivery of VNS to stimulate the Vagus nerve within ten seconds of controlling the delivery of FES evoking the intended movement.

12. The method of claim 9,
    wherein the intended movement is the instructed movement, and
    wherein the determined movement of the extremity does not match the instructed movement.

* * * * *